United States Patent [19]

Guina

[11] Patent Number: 4,764,332
[45] Date of Patent: Aug. 16, 1988

[54] SEALING ELEMENT AND METHOD FOR HYDROTESTING OF NUCLEAR REACTOR TUBULAR ELEMENTS

[75] Inventor: Milan M. Guina, Brussels, Belgium

[73] Assignee: Westinghouse Electric Corp., Pittsburgh, Pa.

[21] Appl. No.: 891,026

[22] Filed: Jul. 31, 1986

[51] Int. Cl.$^4$ .............................................. G21C 13/00
[52] U.S. Cl. .................................. 376/203; 376/245; 138/89; 73/49.5
[58] Field of Search ........................... 138/89; 73/49.5; 376/203, 204, 245, 250

[56] References Cited

U.S. PATENT DOCUMENTS

| | | | |
|---|---|---|---|
| 1,569,875 | 1/1926 | Nixon | 138/89 |
| 2,431,778 | 12/1947 | Sosaya | 138/89 |
| 3,036,601 | 5/1962 | Fabian, Jr. et al. | 138/89 |
| 3,119,177 | 1/1964 | Knecht | 138/89 |
| 3,893,487 | 7/1975 | Engelking | 138/89 |

Primary Examiner—Deborah L. Kyle
Assistant Examiner—Richard L. Klein
Attorney, Agent, or Firm—D. C. Abeles

[57] ABSTRACT

A pipe end sealing element for use in hydrotesting of plain end pipes, such as instrument tubes of a nuclear reactor, and a method of hydrotesting of such plain end pipes. The pipe sealing element comprises a hollow tubular member with a bevelled flange at one end and a threaded portion at the other end, a hollow conical bushing of decreasable interior diameter having a bevelled surface complementary to the bevelled surface of the tubular member, a sealing plug and threaded bolt engageable with the threaded portion of the hollow tubular member. The hollow tubular member is placed about the open end of the pipe, with the threaded portion thereof adjacent and beyond the pipe end, and inserting the conical bushing into the hollow tubular member about the pipe wall. The sealing plug is placed on the pipe end and the threaded bolt engaged with the threads of the hollow tubular member. By advancing the threaded bolt towards the sealing plug, the conical bushing is decreased in interior diameter, by axial sliding of the bevelled surface of flange of the tubular member along the bevelled surface of the conical member. After a predetermined seal is effected, a fluid is introduced into the other end of the pipe to a predetermined pressure to test the pipe.

17 Claims, 4 Drawing Sheets

SEALING ELEMENT AND METHOD FOR HYDROTESTING OF NUCLEAR REACTOR TUBULAR ELEMENTS

BACKGROUND OF THE INVENTION

The hydrotesting of pipes or tubular elements, such as those found in a nuclear reactor, is often a time consuming operation and suitable sealing elements are not readily available, especially for plain end pipes without threads. In hydrotesting threaded pipes, it is, of course, possible to thread a cap on to the end of the pipe to seal the same and then subject the pipe to pressurized water. In testing of plain end pipes, however, suitable sealing elements are not available. While one type of sealing element for a plain end pipe uses a rubber expandable plug, that is inserted into the pipe to seal the same upon expansion, such as existing device does not withstand hydrotesting at high pressures, such as about 3200 pounds pre square inch gauge, that are required for certain tubular elements of nuclear reactors.

In instances where leakage may occur in tubular elements of a nuclear reactor, it is highly advantageous to be able to test the tubular elements themselves, without having to subject the complete reactor vessel to such hydrotesting.

It is an object of the present invention to provide a pipe end sealing element usable for hydrotesting of plain end pipes.

It is another object of the present invention to provide a method for hydrotesting of a pipe in a nuclear reactor vessel which utilizes the novel pipe end sealing element.

SUMMARY OF THE INVENTION

A pipe end sealing element usable in hydrotesting of plain end pipes, such as those present in a nuclear reactor, comprises a cooperative hollow tubular member, hollow conical bushing of variable interior diameter, a sealing plug, and a threaded bolt. The hollow tubular member is adapted to encircle the end of the pipe and has an inwardly directed flange at one end, the flange having a bevelled surface, and a threaded interior wall at the other end. The hollow conical bushing has an inner surface engageable with the pipe outer surface, and an outer bevelled surface complementary to the bevelled surface of the hollow tubular member flange. A slot is preferably provided through the length of the hollow conical bushing to enable decreasing of the interior diameter thereof by forces acting on the outer surface. The sealing plug has a cylindrical portion insertable into the pipe, with a flange portion that rests on the end of the pipe, while the threaded bolt is engageable with the threaded portion of the hollow tubular member.

The method of hydrotesting of a pipe, such as a pipe in a nuclear reactor, comprises providing the pipe end sealing element, placing the hollow tubular member over the open end of the pipe, with the threaded portion adjacent and beyond the pipe end, and inserting the hollow conical bushing into the hollow tubular member to surround the outer wall of the pipe. With the bevelled surface of the conical bushing in sliding relationship with the bevelled surface of the tubular element flange, the sealing plug is placed in the pipe with the portion thereof resting on the pipe end wall, and the threaded bolt is engaged with the tubular element threads. By advancing the threaded bolt towards the sealing plug, the hollow tubular member is pulled in an axial direction away from the pipe end, and the conical bushing is decreased in its interior diameter so as to grip the pipe outer wall, by axial sliding along the bevelled surfaces. When the seal is thus effected, a fluid is injected at a predetermined pressure into the other end of the pipe and the fluid resistant capability of the pipe determined.

DETAILED DESCRIPTION

The present pipe end sealing element is usable in sealing the end of a plain end pipe, i.e. without threading, and enables hydrotesting of the pipe. The device is especially useful in a method for hydrotesting of an open-end pipe that is situated in a nuclear reactor, so as to preclude the need for hydrotesting the entire reactor vessel, in order to determine the integrity of the open-end pipe.

Figure 1:
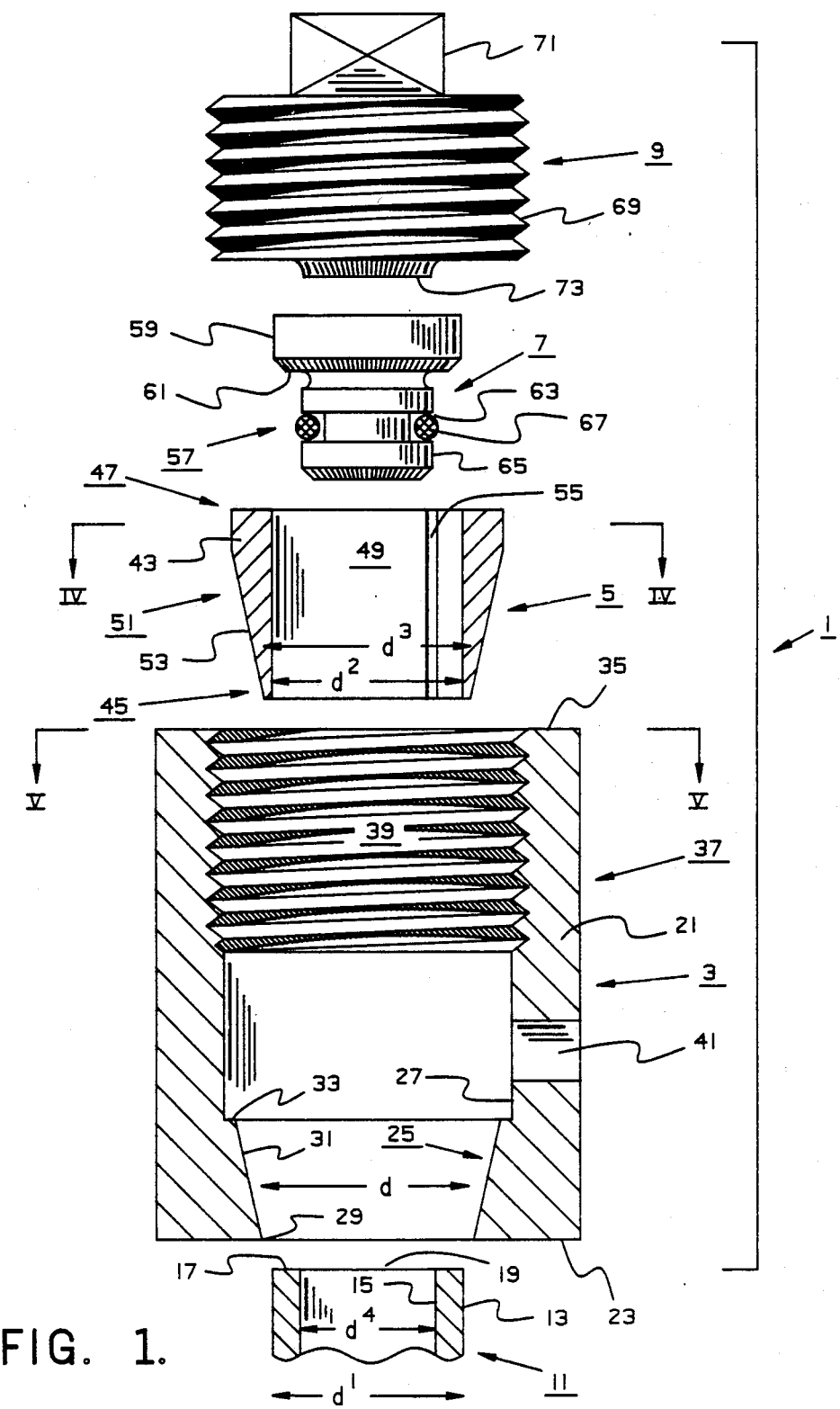
FIG. 1 is an exploded view of the pipe end sealing element, usable in the present method, showing parts thereof in vertical cross-section and parts thereof in elevation, adapted for sealing the open end of a pipe.

Referring now to FIG. 1, the pipe end sealing element 1 comprises a hollow tubular member 3, hollow conical bushing 5, a sealing plug 7 and a threaded bolt 9. The sealing element is usable to seal a pipe 11 having an outer wall 13, inner wall 15 and end wall 17 that surrounds an open end 19 of the pipe 11.

The hollow tubular member 3 is of a size that the same will encircle the open end of the pipe 11, and has an inner diameter d slightly larger than the outer diameter d' of the pipe 11. The wall 21 of the inner tubular member 3, has at one end 23 an inwardly directed flange 25 that extends inwardly from the inner face 27 thereof. The inwardly directed flange 25 terminates at an end 29 which provides the distance d, between facing portions of the flange, and has an inner bevelled surface 31, the bevelled surface diverging from the end 29 towards the inner face 27 of the inner tubular element 3. Preferably, a shoulder 33 is provided about the inner face 27 where the diverging bevelled surface 31 terminates, spaced from the end 29 thereof. At the other end 35 of the hollow tubular member 3, a threaded portion 37 is provided on the inner face 27, having threads 39. An aperture 41 is provided through the wall 21 of the hollow threaded member for use in applying the sealing element to the open end of a pipe, as hereinafter described.

The hollow conical bushing 5, of variable interior diameter, in the nature of a hollow inverted truncated cone, has a wall 43 that forms an apical end 45 and base end 47. At the apical end 45, the inner diameter $d^2$ of the hollow conical bushing 5 is of a value between d and d', while the outer diameter $d^3$ is of a value that is larger than $d^2$, but still with a value between d and d'. The inner surface 49 of the hollow conical bushing 5 is annular, while the outer surface 51 has a bevelled portion 53, the bevel of surface 53 being complementary to the inner bevelled surface 31 of the hollow tubular member 3. A slot 55 is provided in the wall 43 of the hollow conical bushing, extending from the base end 47 to the apical end 45 thereof, such that upon external pressure being applied to the exterior of the bushing, the hollow conical bushing will decrease in interior diameter size.

Sealing plug 7, has a cylindrical portion 57 and flange portion 59, flange portion 59 forming a shoulder 61. The cylindrical portion 57 has an outer diameter which is slightly smaller than the inner diameter $d^4$ of the pipe 11, but has a close fit with the inner wall of the pipe 11 when inserted into the open end thereof. A groove 63 is formed in the outer wall 65 of the cylindrical portion 57 for engagement therein of an O-ring 67.

The threaded bolt 9 has threads 69 thereon, which are engageable with the threads 39 on the threaded portion 37 of the hollow tubular member 3, and a head portion 71 for use in turning of the bolt. Preferably, a raised portion 73 is provided on the threaded bolt 9 on the end opposite the head portion 71.

Figure 2:
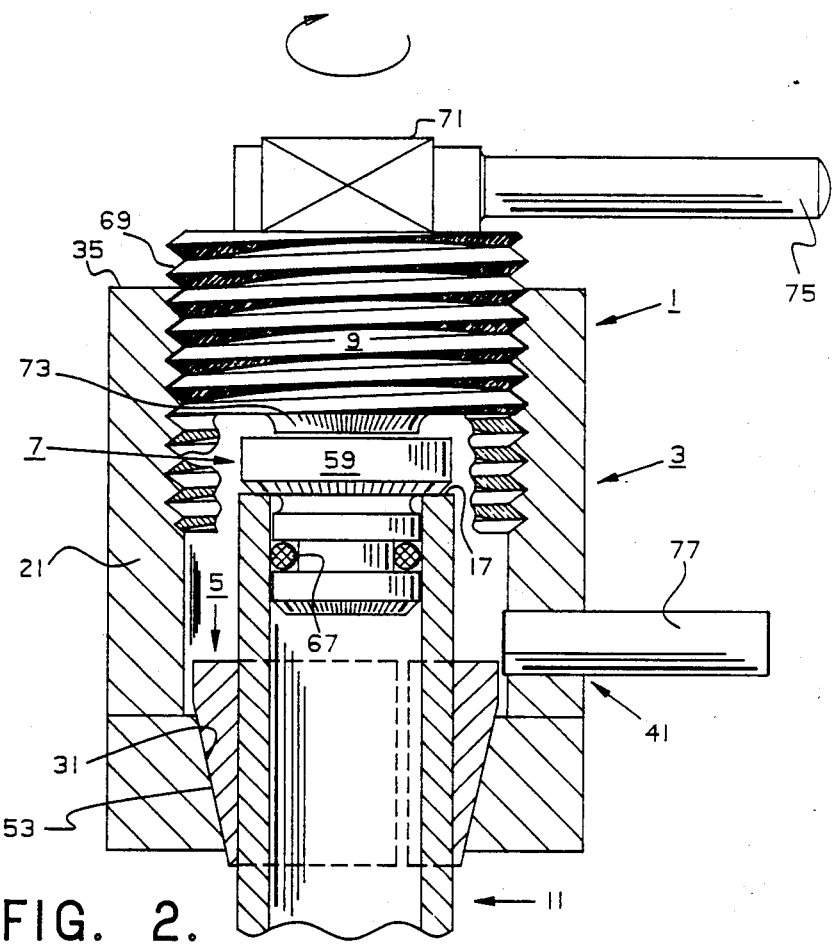
FIG. 2 is a view of the pipe end sealing element of FIG. 1 wherein the element has been engaged with the open end of a pipe, prior to final sealing of said open end.
Figure 5:
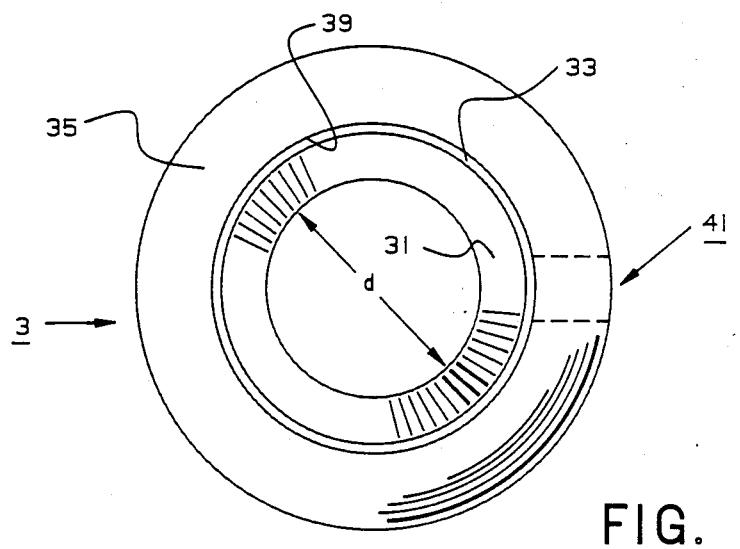
FIG. 5 is a view taken along lines V—V of FIG. 1.

The engagement of the pipe end sealing element 1 with the end of pipe 11 is illustrated in FIG. 2, which illustrates the various components just prior to actual sealing of the open end 19 of pipe 11. In such a position, the hollow tubular member 3 is placed over the open end 19 of the pipe 11 and encircles the same, with the threaded portion 37 thereof adjacent and beyond the open end 19. The conical bushing 5 is next inserted into the hollow tubular member 3 and surrounds the outer wall 13 of the pipe 11, with the bevelled surface 53 on the outer surface 51 of the conical bushing in contact with the bevelled surface 31 on the flange 25 of the hollow tubular member 3. The sealing plug 7 is then placed on the open end 19 of the pipe 11 with the cylindrical portion 57 thereof inserted into the open end 19, and the shoulder 61 of flange 59 seated on the end wall 17 of the pipe 11. The threaded bolt is next engaged by threadedly engaging the threads 69 of the threaded bolt 9 with the threads 39 of the threaded portion 37 of the hollow tubular member 3. The threaded bolt 9 is advanced towards the sealing plug 7 by use of a wrench 75, while the hollow tubular member 3 is prevented from rotation by use of a stop member or rod 77 inserted into the aperture 41 thereof.

Figure 3:
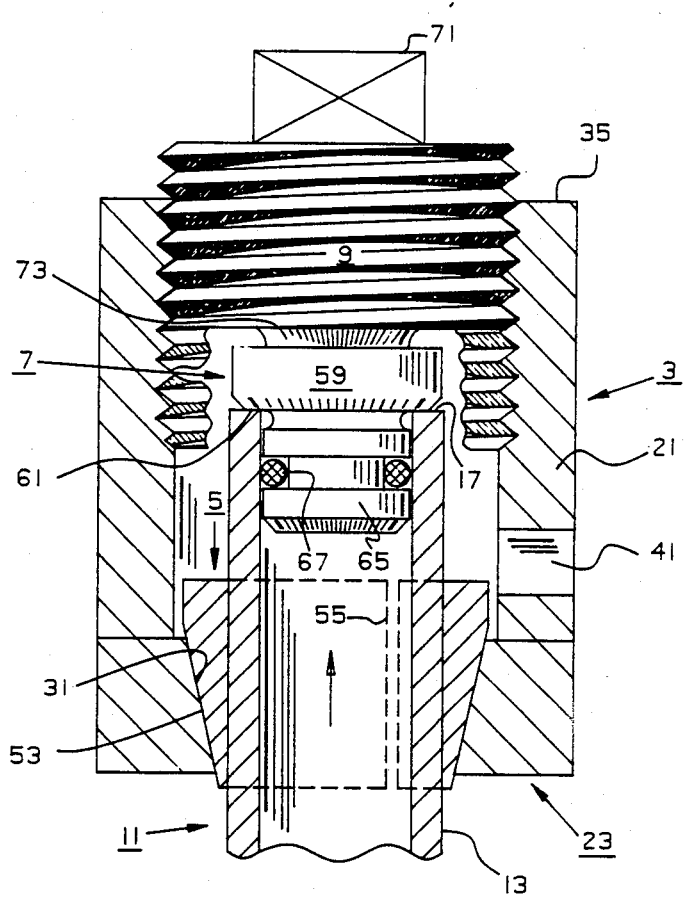
FIG. 3 is a view of the pipe end sealing element of FIG. 1 in sealing engagement with the pipe.
Figure 4:
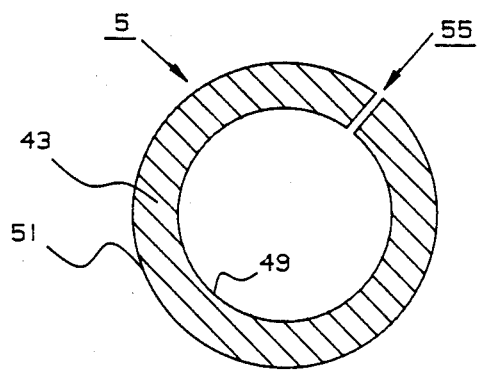
FIG. 4 is a view taken along lines IV—IV of FIG. 1.

In FIG. 2, the raised portion 73 of the threaded bolt 9 has not yet contacted the sealing plug 7. With continued threading, however, the threaded bolt will advance and contact the sealing plug 7, and force the flange 59 thereof into sealing relationship with the end wall 17 of the pipe 11. Upon continued rotation of the threaded bolt 9, the hollow tubular element 3 will be drawn, in an axial direction, towards the bolt 9, and the flange 25 of the hollow tubular element, along bevelled surface 31, will slide along the complementary bevelled surface 53 of the conical bushing 5, as indicated by the arrow in FIG. 3. This sliding movement will cause the conical bushing 5 to decrease in interior diameter and tightly grip the outer wall 13 of the pipe 11, while the sealing plug 7 is held firmly in sealing contact with the end wall 17 of the pipe 11. Upon such securement, as illustrated in FIG. 3, the open end 19 of pipe 11 is completely sealed. By torquing of the threaded bolt 9, the conical bushing 5 applies contact pressure on the pipe 11, so that a sealing relationship is achieved by friction between the conical bushing 5 and the pipe 11. The torque required will be dependent upon the hydrostatic pressure to be exerted on the pipe 11, and is calculated in order to prevent high external stresses on the pipe, as well as to have a sufficient margin below the load that would tend to separate the sealing device from its sealing relationship.

The pipe end sealing element may be produced from various materials depending upon the application of its use. The components may, for example, be formed of carbon steel, stainless steel, other metals, or hard plastics, depending on the application, temperature and pressure to which they will be exposed. The O-ring is normally of a rubber or plastic material, but may be of a metallic substance where high temperatures are present. The pipe sealing element may, of course, be fabricated in various sizes so as to be usable with a variety of sizes of pipe.

Figure 6:
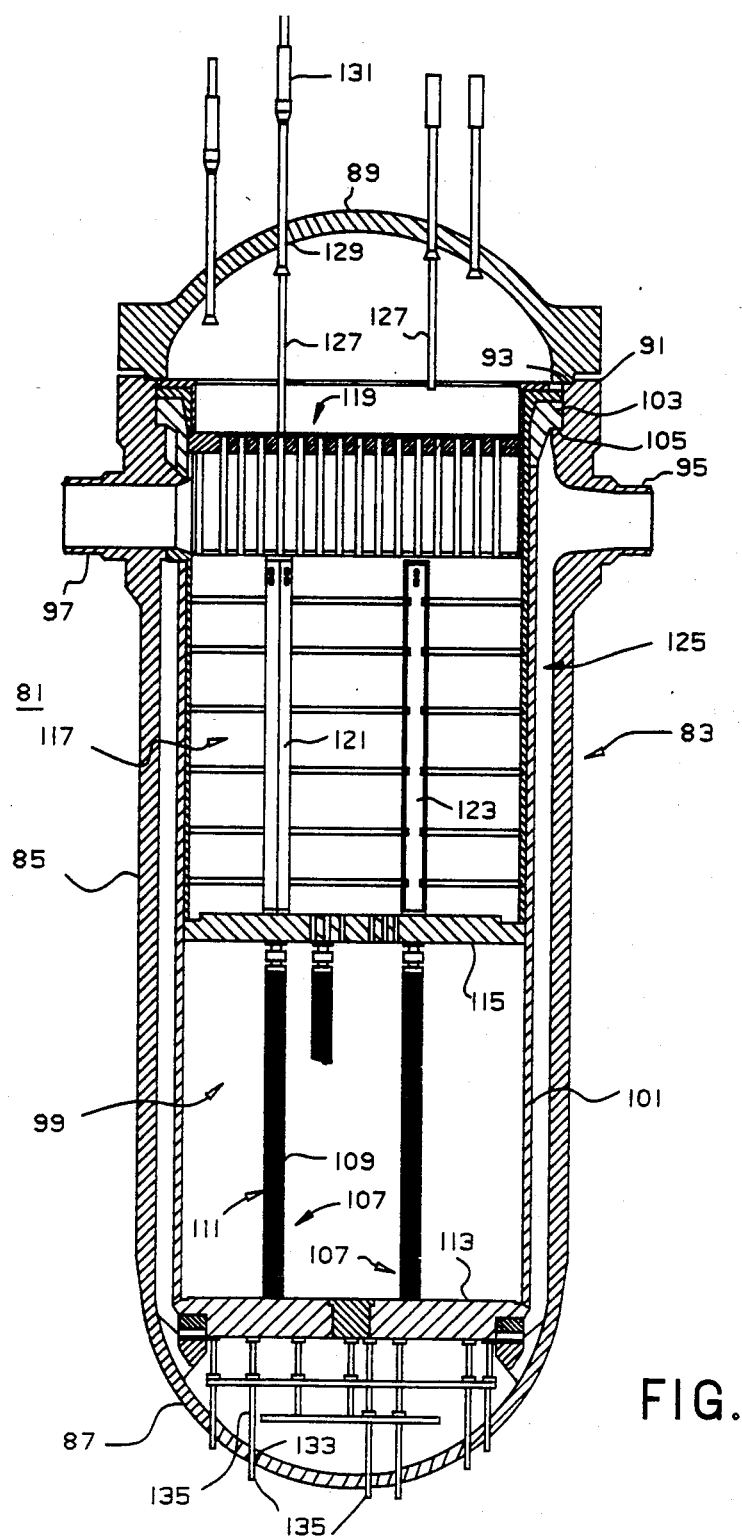
FIG. 6 is a longitudinal cross-sectional view of a representative nuclear reactor with which the present method may be used to hydrotest a pipe thereof.

The pipe end sealing element is especially useful in the hydrotesting of pipes present in a nuclear reactor, such as instrument tubes in a pressurized water reactor. As illustrated in FIG. 6, a pressurized water reactor 81 typically includes a cylindrical pressure vessel 83 that comprises an outer pressure resistant wall 85, closed at the bottom by a bottom wall 87 of a hemispherical contour. The vessel is closed at the top by a flanged, dome-shaped head 89, which is secured, such as by bolts, to the top edge 91 of the pressure resistant wall 85, preferably seated in a channel 93 about the wall 85. The pressure resistant wall 85 has at least one inlet nozzle 95 and at least one outlet nozzle 97 distributed about its periphery, with a pair of each of such nozzles usually provided.

A nuclear core 99 is supported in the lower region of the vessel 83, the core being supported in spaced relationship to the bottom wall 87 by a core barrel 101, the core barrel 101 having a flange 103 which rests on a ledge 105 in the inner surface of the pressure resistant wall 85. The core includes a series of fuel assemblies 107 and thimbles 109 for receiving control rods, not shown, with at least one such thimble 111 adapted for insertion therein of an instrument for monitoring the operation of the core. The fuel assemblies and thimbles are mounted between a lower core plate 113 and an upper core plate 115. The control rods, as is known, may contain rod clusters of high or low absorption cross-section for neutrons, and water displacement rod clusters, and serve to reduce the thermal power of the reactor, or otherwise control the same, through monitoring by use of the instrument in the dedicated thimble therefore, or to shutdown the reactor.

In the upper region of vessel 83, the upper internals 117 may have an associated calandria structure 119. The upper internals 117 include vertical guides 121 for control rods and vertical guides 123 for water displacement rods, while the calandria structure 119 is disposed thereabove. The core 99, upper internals 117, and calandria structure 119 are mounted generally coaxially within the vessel 83. An annulus 125 between the core barrel 101 and the pressure resistant wall 85 provides for communication between the inlet nozzles 95 and the lower end of the core 99. Drive rods 127 from the control rods extend through head penetrating adaptors 129 in the dome-shaped head and then through the calandria structure 119. Drive rod mechanisms 131 are used to properly position the control rods. Coolant enters through inlet nozzles 95 and flows downwardly through annulus 125 to the bottom wall 87 and then upwardly through the core 99, upper internals 117 and into the calandria structure 119, from which it flows transversely to, and outwardly from, the outlet nozzles 97.

The instrument leads to instruments in thimbles 111 extend through a plurality of adapters 133 in the bottom wall 87, through tubular elements or pipes 135 which cooperate with apertures (not shown) in the lower core plate 113, such that readings of the operation of the core may be made externally of the reactor vessel.

When testing of pipes in a nuclear reactor for integrity, such as testing of the tubular elements or pipes 135 after the lower core plate has been removed, the method of the present invention may be used. The present pipe end sealing element is placed over the open end of the pipe to seal the same, as hereinbefore described, and water injected under pressure through the other end of the pipe to a predetermined pressure. If the pipe withstands the pressurized water, the pressure is then released, and the pipe end sealing element removed. The pipes are then suitable for intended use.

What is claimed is:

1. A method for the hydrotesting of an open-end pipe having an end wall, situated within a nuclear reactor pressure vessel, comprising:
   providing a pipe end sealing element having;
   a hollow tubular member, adapted to encircle the open end of the pipe, having an inwardly directed flange at one end thereof, said flange having an inner bevelled surface, and a threaded portion of the inner face of said hollow tubular member at the other end thereof adjacent the end of the pipe;
   a hollow conical bushing having an inner surface engageable with the outer surface of the pipe spaced from the open end thereof, said inner surface having an interior diameter and said bushing having means for varying said interior diameter, and said bushing having an outer bevelled surface complementary to the bevel of the bevelled surface of the flange of the hollow tubular member;
   a sealing plug insertable into the open end of said pipe with a portion thereof resting on the end wall of said pipe; and
   a threaded bolt threadably engageable with the threaded portion of the hollow tubular member;
   placing the hollow tubular member over the open end of the pipe, with the threaded portion thereof adjacent and beyond the open end thereof;
   inserting said hollow conical bushing into said hollow tubular member such that the same surrounds the outer wall of the pipe, with the bevelled surface of the conical bushing in sliding relationship to the bevelled surface on the flange of the hollow tubular member;
   placing said sealing plug on the open end of the pipe;
   engaging said threaded bolt with the threads of the hollow tubular member;
   advancing said threaded bolt towards said sealing plug to contact the same, while preventing rotation of the hollow tubular member, such that the hollow conical bushing is decreased in its interior diameter to grip the outer wall of the pipe, by axial sliding movement of the bevelled surface of the hollow tubular member, and finally hold the sealing plug in sealing contact with the end wall of the pipe; and
   injecting a fluid into said pipe from a location spaced from the end having the sealing element thereof to a predetermined pressure to determine the fluid resistant capability of the wall of said pipe.

2. The method as defined in claim 1 wherein said hollow conical bushing has a base end and an apical end, and a slot therein extending from said base end to said apical end so as to enable decreasing of the interior diameter thereof.

3. The method as defined in claim 1 wherein said hollow tubular member has means thereon for preventing rotation of said hollow tubular member resulting from threading of said bolt into said hollow tubular member.

4. The method as defined in claim 3 wherein said means for preventing rotation of said hollow tubular member comprises an aperture in the wall thereof adapted for insertion therein of a stop member.

5. The method as defined in claim 4 wherein said stop member is a rod insertable into the aperture in said wall.

6. The method as defined in claim 1 wherein said sealing plug has a cylindrical portion insertable into the open end of the pipe and a flange portion adapted to rest on the end wall of a pipe.

7. The method as defined in claim 6 wherein said cylindrical portion has a groove formed in the outer wall thereof, and an O-ring is engaged within said groove.

8. The method as defined in claim 1 wherein said threaded bolt has a head portion adapted for use in turning the bolt and a raised portion on the end thereof opposite the head portion adapted to contact said sealing plug upon threaded engagement of said bolt with said hollow tubular member containing said sealing plug therein.

9. A pipe end sealing element, for use in sealing a pipe for hydrotesting, which pipe has an open end and an end wall thereon, comprising;
   a hollow tubular member, adapted to encircle the open end of the pipe, having an inwardly directed flange at one end thereof, said flange having an inner bevelled surface, and a threaded portion on the inner face of said hollow tubular member at the other end thereof adjacent the end of the pipe;
   a hollow conical bushing having an inner surface engageable with the outer surface of the pipe spaced from the open end thereof, said inner surface having an interior diameter, and said bushing having means for varying said interior diameter, and said bushing having an outer bevelled surface complementary to the bevel of the bevelled surface of the flange of the hollow tubular member;
   a sealing plug insertable into the open end of said pipe, with a portion thereof resting on the end wall of said pipe; and
   a threaded bolt threadably engageable with the threaded portion of the hollow tubular member, whereby upon threading of the bolt into said hollow tubular member, the bevelled surface of the hollow tubular member slides along the bevelled surface of the conical bushing to decrease the interior diameter of the conical bushing and force the conical bushing into further engagement with the outer surface of the pipe, while forcing the sealing plug into sealing relationship with the end of the pipe.

10. The pipe end sealing element as defined in claim 9 wherein said hollow tubular element has means thereon for preventing rotation of said hollow tubular element resulting from threading of said bolt into said hollow tubular member.

11. The pipe end sealing element as defined in claim 10 wherein said means for preventing rotation of said hollow tubular element comprises an aperture in the wall thereof adapted for insertion therein of a stop member.

12. The pipe end sealing element as defined in claim 11 wherein said stop member is a rod insertable into the aperture in said wall.

13. The pipe end sealing element as defined in claim 1 wherein said sealing plug has a cylindrical portion insertable into the open end of the pipe and a flange portion adapted to rest on the end wall of the pipe.

14. The pipe end sealing element as defined in claim 13 wherein said cylindrical portion has a groove formed in the outer wall thereof, and an O-ring is engaged within said groove.

15. The pipe end sealing element as defined in claim 1 wherein said threaded bolt has a head portion adapted for turning the bolt and a raised portion on the end thereof opposite the head portion adapted to contact said sealing plug upon threaded engagement of said bolt with said hollow tubular element containing said sealing plug therein.

16. A pipe end sealing element, for use in sealing a pipe for hydrotesting, which pipe has an open end and an end wall thereon, comprising:
- a hollow tubular member, adapted to encircle the open end of the pipe, having an inwardly directed flange at one end thereof, said flange having an inner bevelled surface, and a threaded portion on the inner face of said hollow tubular member at the other end thereof adjacent the end of the pipe;
- a hollow conical bushing, having a base end and an apical end, and a slot therein extending from said base end to said apical end, said bushing of variable interior diameter having an inner surface engageable with the outer surface of the pipe spaced from the open end thereof, and an outer bevelled surface complementary to the bevel of the bevelled surface of the flange of the hollow tubular member;
- a sealing plug having a cylindrical portion insertable into the open end of the pipe and a flange portion adapted to rest on the end wall of the pipe, said cylindrical portion having a groove formed in the outer wall thereof, and an O-ring engaged within said groove; and
- a threaded bolt threadably engageable with the threaded portion of the hollow tubular member, whereby upon threading of the bolt into said hollow tubular member, the bevelled surface of the hollow tubular member slides along the bevelled surface of the conical bushing to decrease the interior diameter of the conical bushing and force the conical bushing to further engagement with the outer surface of the pipe, while forcing the sealing plug into sealing relationship with the end of the pipe.

17. A pipe end sealing element, for use in sealing a pipe for hydrotesting, which pipe has an open end and an end wall thereon, comprising:
- a hollow tubular member, adapted to encircle the open end of the pipe, having an inwardly directed flange at one end thereof, said flange having an inner bevelled surface, and a threaded portion on the inner face of said hollow tubular member at the other end thereof adjacent the end of the pipe;
- a hollow conical bushing having an inner surface engageable with the outer surface of the pipe spaced from the open end thereof, said inner surface having an interior diameter, and said bushing having a base end and an apical end, and a slot therein extending from said base end to said apical end so as to enable decreasing of the interior diameter thereof, and said bushing having an outer bevelled surface complementary to the bevel of the bevelled surface of the flange of the hollow tubular member;
- a sealing plug insertable into the open end of said pipe, with a portion thereof resting on the end wall of said pipe; and
- a threaded bolt threadably engageable with the threaded portion of the hollow tubular member, whereby upon threading of the bolt into said hollow tubular member, the bevelled surface of the hollow tubular member slides along the bevelled surface of the conical bushing to decrease the interior diameter of the conical bushing and force the conical bushing into further engagement with the outer surface of the pipe, while forcing the sealing plug into sealing relationship with the end of the pipe.

* * * * *